(12) United States Patent
Yoon et al.

(10) Patent No.: US 11,071,973 B2
(45) Date of Patent: Jul. 27, 2021

(54) TRANSITION METAL-BASED HETEROGENEOUS CARBONYLATION REACTION CATALYST AND METHOD FOR PREPARING LACTONE OR SUCCINIC ANHYDRIDE USING CATALYST

(71) Applicant: KOOKMIN UNIVERSITY INDUSTRY ACADEMY COOPERATION FOUNDATION, Seoul (KR)

(72) Inventors: Sungho Yoon, Seoul (KR); Senkuttuvan Rajendiran, Seoul (KR); Jianwei Jiang, Seoul (KR); Kwang Ho Park, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 16/963,713

(22) PCT Filed: Jan. 22, 2019

(86) PCT No.: PCT/KR2019/000876
§ 371 (c)(1),
(2) Date: Jul. 21, 2020

(87) PCT Pub. No.: WO2019/143220
PCT Pub. Date: Jul. 25, 2019

(65) Prior Publication Data
US 2020/0391192 A1    Dec. 17, 2020

(30) Foreign Application Priority Data
Jan. 22, 2018  (KR) ........................ 10-2018-0007620

(51) Int. Cl.
*B01J 31/16*    (2006.01)
*B01J 37/00*    (2006.01)
*C07D 305/12*   (2006.01)
*C07D 307/60*   (2006.01)

(52) U.S. Cl.
CPC ............... *B01J 31/16* (2013.01); *B01J 37/00* (2013.01); *C07D 305/12* (2013.01); *C07D 307/60* (2013.01)

(58) Field of Classification Search
CPC ........................................ B01J 31/16
See application file for complete search history.

(56) References Cited

FOREIGN PATENT DOCUMENTS

| KR | 10-2012-0023643 A | 3/2012 |
| KR | 10-2013-0091891 A | 8/2013 |
| KR | 10-2016-0097062 A | 8/2016 |
| KR | 10-2017-0134374 A | 12/2017 |

OTHER PUBLICATIONS

Taniguchi, M. et al., Synthesis of oligo(p-phenylene)-linked dyads containing free base, zinc(II) or thallium(III) porphyrins for studies in artificial photosynthesis, TETRAHEDRON. 2010, pp. 5549-5565, vol. 66.
Sungho Yoon et al., C1 Gas Refinery, Kookmin University, Oct. 30, 2017.
Korea Intellectual Property Office, Notice of Refusal to Grant in counterpart KR 10-2018-0007620 dated May 10, 2019.
Korea Intellectual Property Office, Notice of Allowance in counterpart KR 10-2018-0007620 dated Oct. 14, 2019.
International Search Report for PCT/KR2019/000876 dated Apr. 24, 2019 [PCT/ISA/210].

*Primary Examiner* — Golam M Shameem
(74) *Attorney, Agent, or Firm* — Sughrue Mion, PLLC

(57) ABSTRACT

The present invention relates to a transition metal-based heterogeneous carbonylation reaction catalyst that has an excellent catalytic activity and selectivity in the carbonylation reaction and is easily separated from a product, by crosslinking polymerizing a transition metal-based homogeneous catalyst unit through a Friedel-Craft reaction; and a method for preparing lactone using the same. The transition metal-based heterogeneous carbonylation reaction catalyst allows to produce lactone or succinic anhydride with an epoxide compound while showing a high selectivity, and can be applied in industrial very usefully due to easy separation from the product and thus reusing thereof.

13 Claims, 5 Drawing Sheets

[Fig. 1]
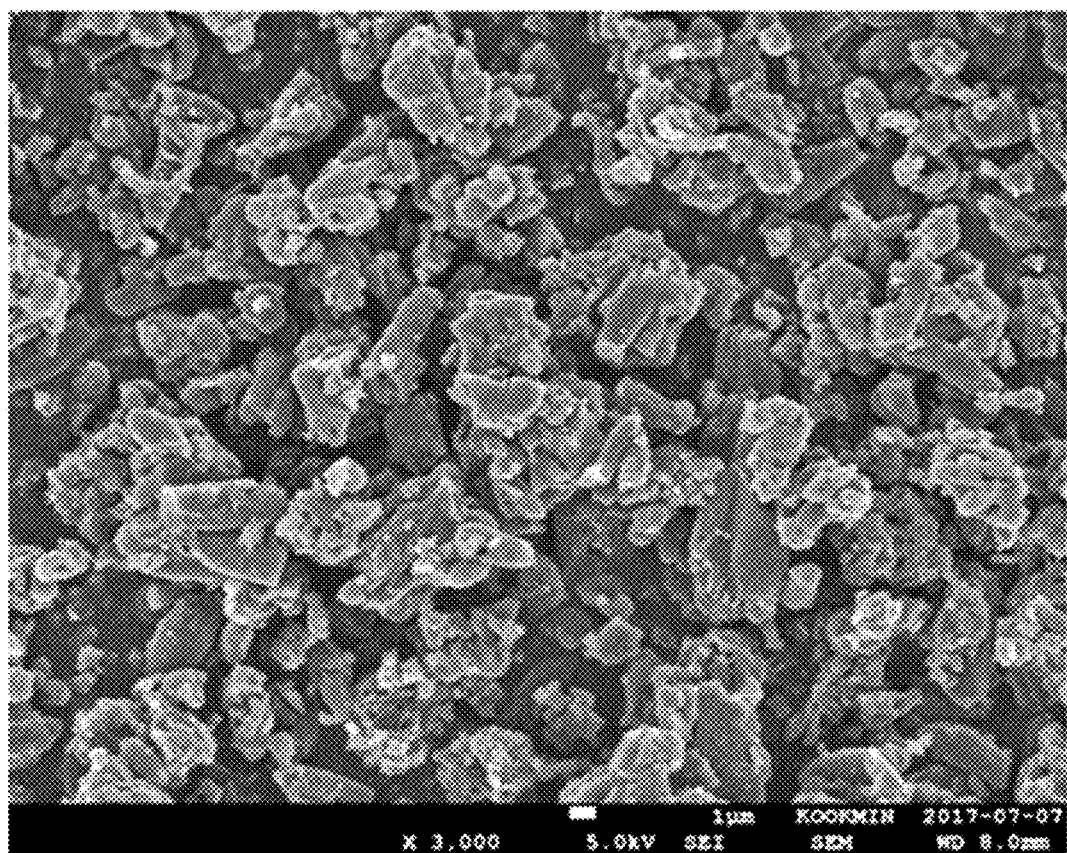

[Fig. 2]
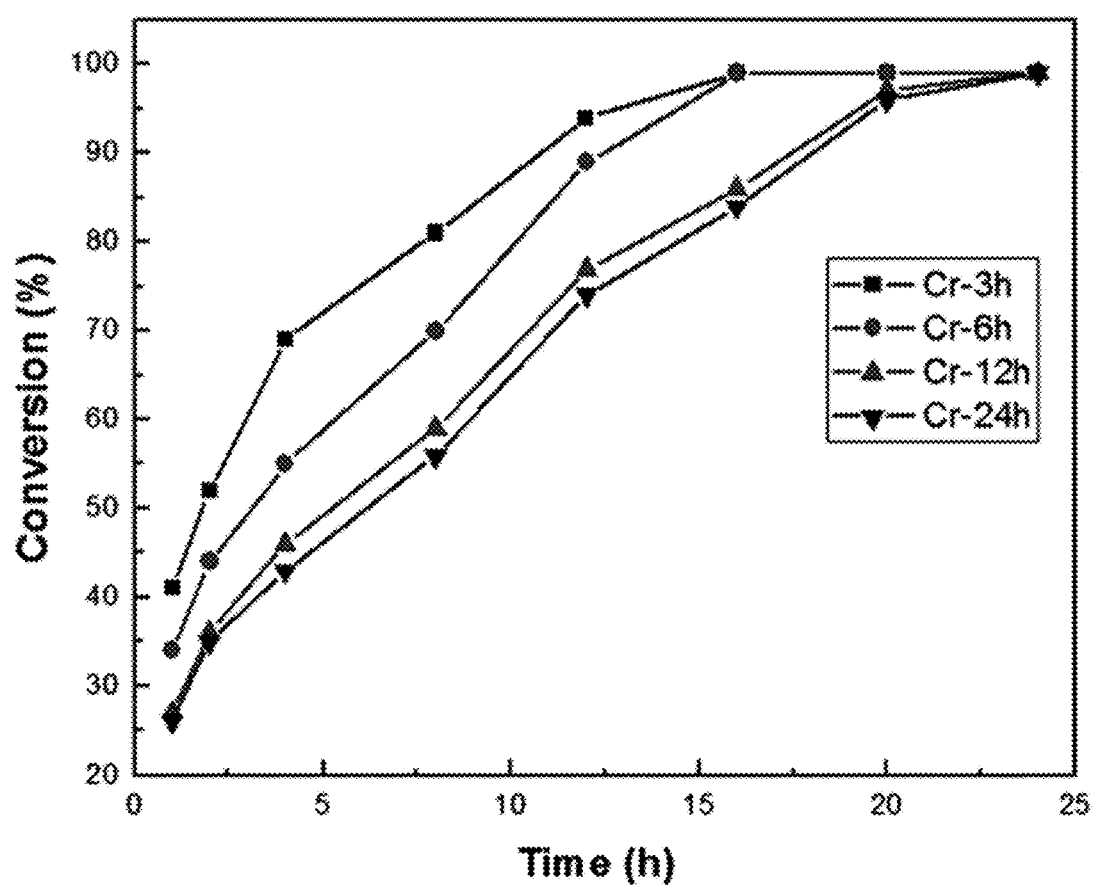

[Fig. 3]
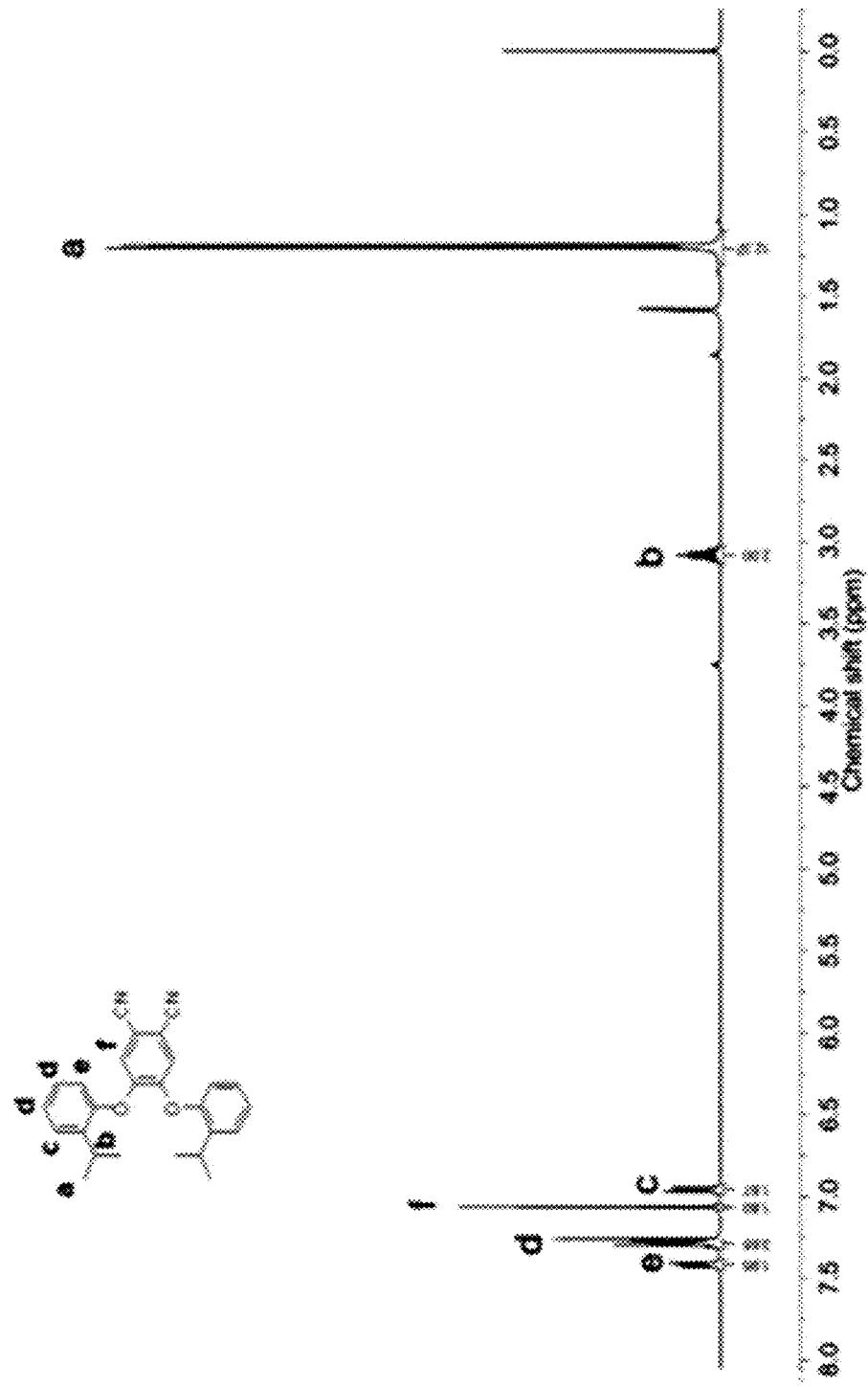

[Fig. 4]
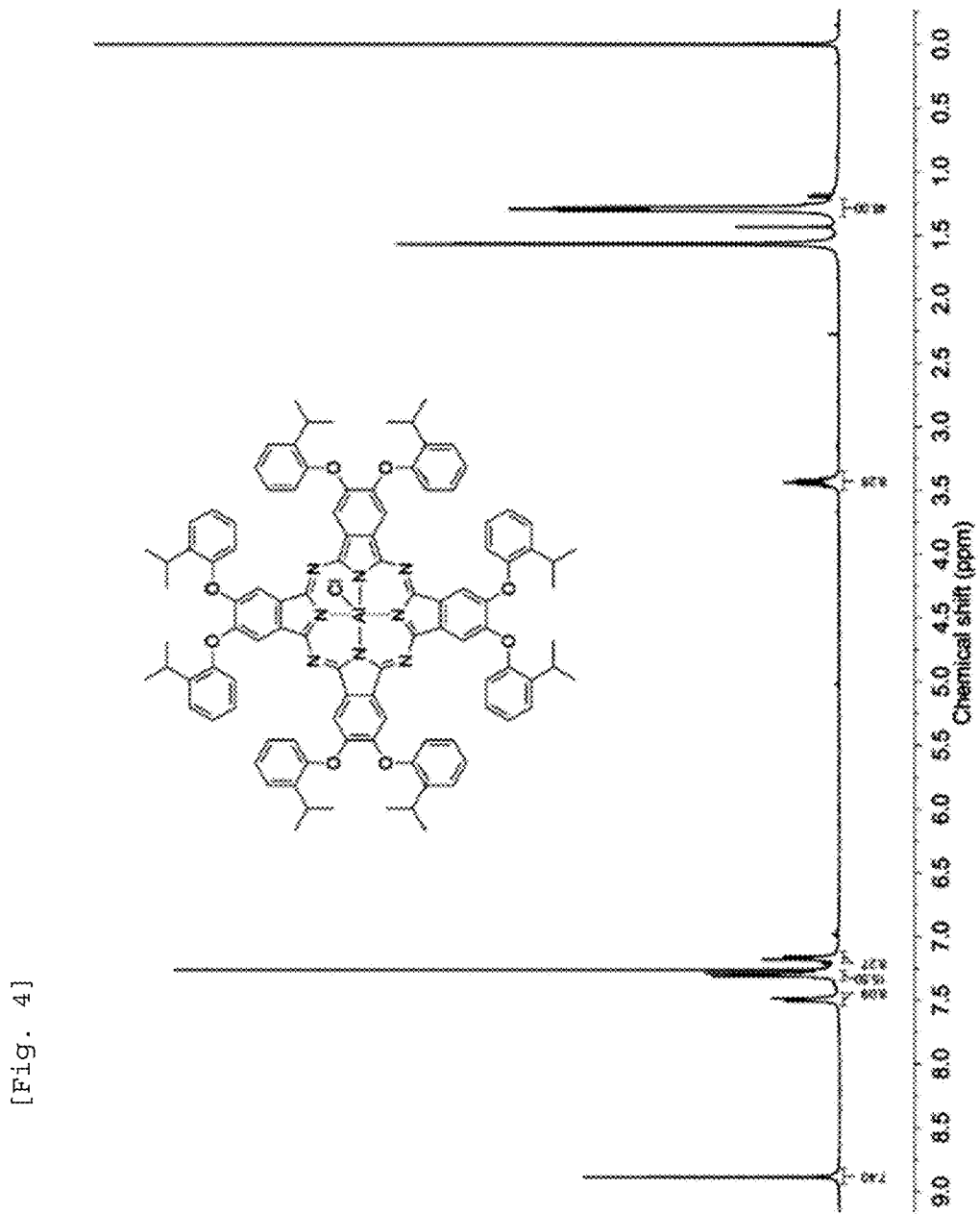

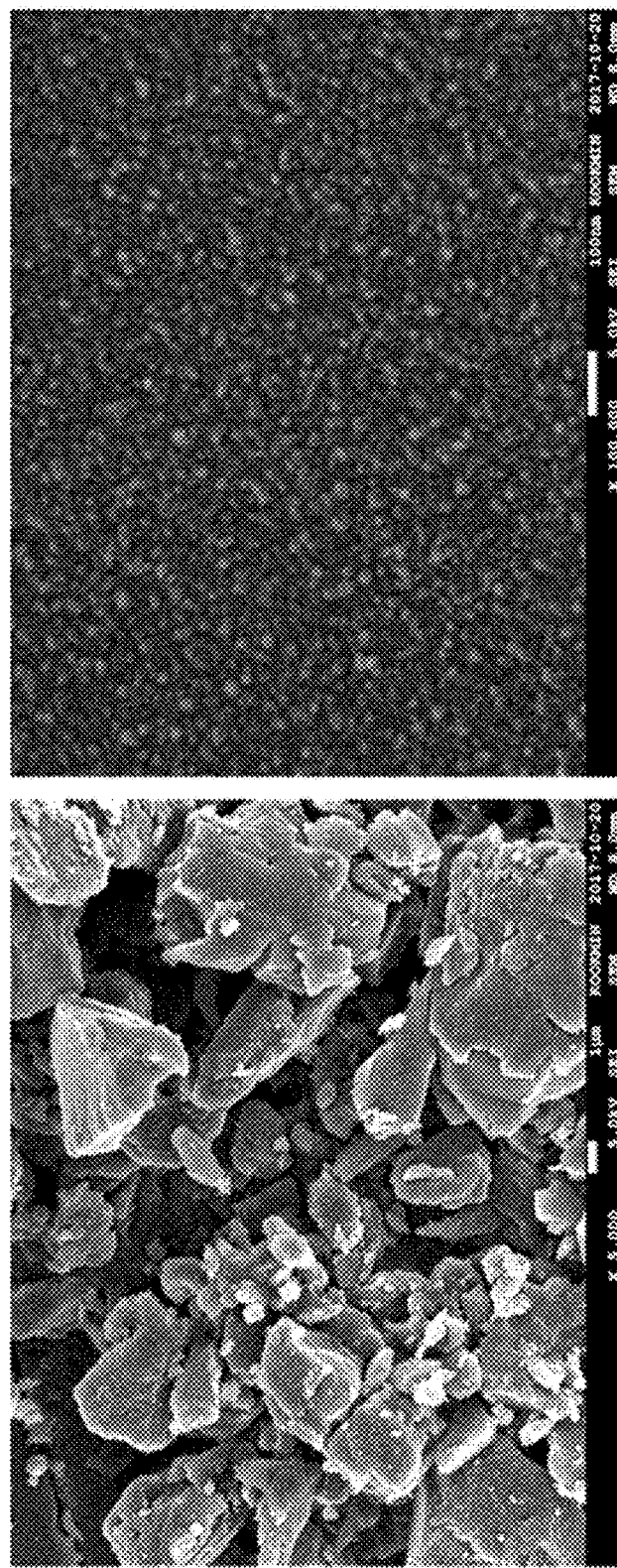
[Fig. 5]

TRANSITION METAL-BASED HETEROGENEOUS CARBONYLATION REACTION CATALYST AND METHOD FOR PREPARING LACTONE OR SUCCINIC ANHYDRIDE USING CATALYST

CROSS REFERENCE TO RELATED APPLICATIONS

This application is a National Stage of International Application No. PCT/KR2019/000876 filed Jan. 22, 2019, claiming priority based on Korean Patent Application No. 10-2018-0007620 filed Jan. 22, 2018.

TECHNICAL FIELD

The present invention relates to a transition metal-based heterogeneous carbonylation reaction catalyst and a method for preparing lactone or succinic anhydride using the same. More specifically, the present invention is directed to a transition metal-based heterogeneous carbonylation reaction catalyst that has an excellent catalytic activity and selectivity in the carbonylation reaction and is easily separated from a product, by crosslinking and polymerizing a transition metal-based homogeneous catalyst unit through a Friedel-Crafts reaction; and a method for preparing lactone or succinic anhydride using the same.

BACKGROUND OF THE INVENTION

β-lactone is an important intermediate of ring-opening polymerization to form poly(β-hydroxy alkanoate), which is a naturally occurring biodegradable (Muller, H.-M. et al., *Angew. Chem.*, Int. Ed. 1993, 32, 477; Sudesh, K. et al., *Prog. Polym. Sci.* 2000, 25, 1503) and thermoplastic polyester (Gerngross, T. U. et al., *Sci. Am.* 2000, 283(2), 36-41; Bronco, S. et al., Macromolecules 1994, 27, 4436; Jiang, Z. et al., *J. Am. Chem. Soc.* 1995, 117, 4455). Many synthetic methods are available for preparing the β-lactone (Nozaki, K. et al., *J. Am. Chem. Soc.* 1995, 117, 9911; Chang, B.-H. et al., *J. Polym Prepr.* (*Am. Chem. Soc., Div. Polym. Chem.*) 1995, 36(2), 146; Yokouchi, M. et al., *J. Polym. Sci.* 1976, 14, 81; Kurcok, P. et al., Macromolecules 1992, 25, 2017; Hori, Y. et al., *Macromolecules* 1993, 26, 5533). Among them, the catalytic ring-opening carbonylation reaction of epoxide is receiving much attention because it can generate an enantiopure β-lactone.

The carbonylation of the epoxide based the transition metal is of great interest as an important heterocycle in various fields of polymer and synthetic chemistry to produce the β-lactone. Both homogeneous and heterogeneous catalyst systems have been used in the method for producing the β-lactone for decades. Most of these catalyst systems were limited due to catalyst recycling and recovery issues.

Coates et al. has recently reported that a homogeneous porphyrin cobalt complex showed an excellent conversion rate of the epoxide to lactone with a TON of 10,000. Further, a chromium chloride cobalt complex exhibited the excellent conversion rate of the epoxide to the lactone under an ambient condition. Furthermore, these catalysts are decomposed during separation of a product and the recovery of the catalysts is poor so that they are not recycled, which are significantly limited to practically use in the industrial process. In addition, continuous supply of the catalyst is not cost effective in view of a large scale. In order to solve those problems, an active site of the homogeneous catalyst on a solid support developed up to now was non-homogenized, which was found to be preferable by easy separation and high catalytic efficiency (Chen, Y. et al., *ChemCatChem*, 2017, 9, 767). In addition, a heterogeneous catalyst based on a material called a metal organic framework (MOF) was studied (Park, H. D. et al., *ACS Cent. Sci.*, 2017, 3, 444; Peters, A. W. et al., *ACS Cent. Sci.* 2017, 3, 367). The MOF is composed of a combination of a ligand and a metal, and it has been pointed out that the MOF has a weak durability against chemical actions such as acid/base and heat.

In recent years, covalent triazine frameworks (CTFs) with high surface area, stability, large pore volume, and structural adjustability have received much attention as the heterogeneous catalyst support (Cote, A. et al., Science 2005, 310, 1166; Uribe-Romo, F. et al., *J. Am. Chem. Soc.* 2011, 133, 11478; Kandambeth, S. et al., *J. Am. Chem. Soc.* 2012, 134, 19524; Ding, Y. S. et al., *J. Am. Chem. Soc.* 2011, 133, 19816) (Beaudoin, D. et al., *J. Nat. Chem.* 2013, 5, 830; Katekomol, P. et al., *Chem. Mater.* 2013, 25, 1542; Chan-Thaw, C. E. et al., *Abstr. Pap. Am. Chem. Soc.* 2010, 240; Chan-Thaw, C. E. et al., *Nano Lett.* 2010, 10, 537; Kailasam, K. et al., *Chem. Mater.* 2010, 22, 428; Hug, S. et al., J. Mater. Chem. 2012, 22, 13956). In particular, bipyridine-based CTF contains a bipyridine ligand motif within a pore wall of the framework, and has the potential that forms a complex with a tendency to an N—N coordination (Park, K. et al., *ChemSusChem.* 2015, 8, 3410).

However, development of a high-efficient, renewable, heterogeneous catalyst having the function of the homogeneous catalyst to increase the TON of lactone remains a difficult task.

Thus, the present inventors have tried to solve the problem that mass production of the β-lactone through the carbonylation of the epoxide is difficult because the homogeneous catalyst is hardly separated from the product, making it difficult to reuse. As a result, the present inventors have found that a porous organic material (hereinafter, referred to as POM), which is implemented by crosslinking and polymerizing the transition metal-based homogeneous catalyst unit through the Friedel-Crafts reaction, has not only excellent thermal/chemical/acidic/basic stabilities and a high selectivity of 99% or higher, but also makes possible it to prepare lactone and succinic anhydride by carbonylating ethylene oxide or other epoxides and is easy to separate from the product, thereby completing the present invention.

SUMMARY OF THE INVENTION

An object of the present invention is to provide a transition metal-based heterogeneous carbonylation reaction catalyst that is stable to an acid, a base and a temperature, and is easy to separate from a products, and a method for preparing the same.

Another object of the present invention is to provide a method for preparing lactone or succinic anhydride that exhibits a catalytic efficiency and selectivity higher than a conventional catalyst including a homogeneous system, using the transition metal-based heterogeneous carbonylation reaction catalyst.

In order to achieve the above objects, the present invention provides a transition metal-based heterogeneous carbonylation reaction catalyst, characterized in that the transition metal-based homogeneous catalyst unit represented by chemical formula (1) below is bonded through a Friedel-Crafts reaction:

$$M(L-R_n)X \qquad \text{[Chemical formula (1)]}$$

In the chemical formula (1), M is a transition metal of Al, Ir, Pt, Pd, Ru, Rh, Ni, Fe, Cu, V, Co, Cr, Au, Re, W, Zr, Mo, Ti, Th or Si, L is a ligand having three or more metal coordination numbers, R is a phenyl ring capable of carrying out the Friedel-Crafts reaction, n is an integer of 2 or more, and X is a counter anion of $[Co(CO)_4]^-$.

The present invention also provides a method for preparing a transition metal-based heterogeneous carbonylation reaction catalyst, the method comprising the steps of:

(a) synthesizing a ligand compound having three or more metal coordination numbers to which a phenyl ring capable of carrying out a Friedel-Crafts reaction is bound;

(b) synthesizing a transition metal-based homogeneous catalyst unit by reacting the ligand compound with a transition metal compound; and (c) preparing the transition metal-based heterogeneous carbonylation reaction catalyst by performing the Friedel-Crafts reaction of the transition metal-based homogeneous catalyst unit and reacting it with a counter anion-containing compound.

The present invention also provides a method for producing lactone or succinic anhydride, characterized in that epoxide and carbon monoxide are carbonylated using the transition metal-based heterogeneous carbonylation reaction catalyst to produce the lactone or the succinic anhydride.

BRIEF DESCRIPTION OF THE DRAWINGS

FIG. 1 is a SEM photograph of a porphyrin-based heterogeneous catalyst prepared according to an embodiment of the present invention.

FIG. 2 is a graph showing a conversion rate of lactone that varies with a reaction time of a porphyrin-based heterogeneous catalyst prepared according to an embodiment of the present invention.

FIG. 3 is a $^1$H NMR graph of a ligand compound prepared according to an embodiment of the present invention.

FIG. 4 is a $^1$H NMR graph of an aluminum phthalocyanine derivative compound prepared according to an embodiment of the present invention.

FIG. 5 is a SEM photograph of an aluminum phthalocyanine-based POM prepared according to an embodiment of the present invention (left: high magnification, right: low magnification).

DETAILED DESCRIPTION OF THE INVENTION AND CONCRETE EMBODIMENT

Unless defined otherwise, all technical and scientific terms used herein have the same meanings as those commonly understood by a person skilled in the art to which the present invention pertains. In general, the nomenclature used in this specification and the experimental methods described below are well known and commonly used in the present technical field.

According to the present invention, it was found that a porous organic material (POM) implemented by crosslinking and polymerizing a transition metal-based homogeneous catalyst unit through a Friedel-Crafts reaction is excellent in thermal/chemical/acidic/basic stabilities and is easily separated from a product.

Accordingly, in an aspect, the present invention relates to a transition metal-based heterogeneous carbonylation reaction catalyst, characterized in that a transition metal-based homogeneous catalyst unit represented by chemical formula (1) below is bonded through the Friedel-Crafts reaction:

$$M(L-R_n)X \qquad \text{[Chemical formula (1)]}$$

In the chemical formula (1), M is a transition metal of Al, Ir, Pt, Pd, Ru, Rh, Ni, Fe, Cu, V, Co, Cr, Au, Re, W, Zr, Mo, Ti, Th or Si, L is a ligand having three or more metal coordination numbers, R is a phenyl ring capable of carrying out the Friedel-Crafts reaction, n is an integer of 2 or more, and X is a counter anion of $[Co(CO)_4]^-$.

The present invention is characterized in that the homogeneous catalyst unit is implemented with the POM by bonding the catalyst unit through the Friedel-Crafts reaction. Unlike a MOF (metal organic framework), the POM is composed of a covalently bonded framework and has high thermal/chemical/acid/basic stabilities. In addition, a porosity of the POM has the effect that increases the mass transfer of materials in the process and can introduce the materials into a gas phase reaction. Contrary to this, the MOF, which is frequently used in the prior art, is composed of a bond of a ligand and a metal and has a weak durability against chemical actions such as acid/base and heat.

The POM of the present invention may be referred to strictly as a covalent organic framework (COF). The COF is stable even at a temperature of 400° C. or higher, and has the porosity of 1000 m³/g or higher and a pore radius of 2 nm or higher.

The POM is very important due to its chemical and thermal stability and adjustable porosity, which makes it possible to use the POM as a promising platform for industrial applications. Therefore, the transition metal-based homogeneous catalyst unit such as porphyrin cobaltate, salen cobaltate, salphen cobaltate, and phthalocyanine cobaltate can be fixed to the MOF material to synthesize a catalyst having high industrial value.

Meanwhile, the Friedel-Crafts reaction means a reaction in which an aromatic compound and alkyl halide or acyl halide are reacted in the presence of aluminum halide anhydride to perform alkylation or acylation, respectively.

In the present invention, the L may be phthalocyanine, porphyrin, salen, or salphen.

In the present invention, the R may be represented by chemical formula (2) below:

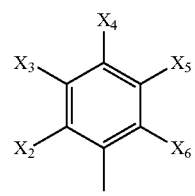

[Chemical formula (2)]

In the chemical formula (2), $X_2$ to $X_6$ are each independently selected from the group consisting of a hydrogen, $C_1$ to $C_{20}$ alkyl group, $C_2$ to $C_{20}$ alkenyl group, $C_2$ to $C_{20}$ alkynyl group, $C_6$ to $C_{40}$ aryl group, a phenoxy group, $C_1$ to $C_{20}$ alkoxy group, and a halogen group, provided that at least one of them should be a hydrogen.

In the present invention, the transition metal-based heterogeneous carbonylation reaction catalyst can be preferably represented by chemical formula (3) below:

[Chemical formula (3)]

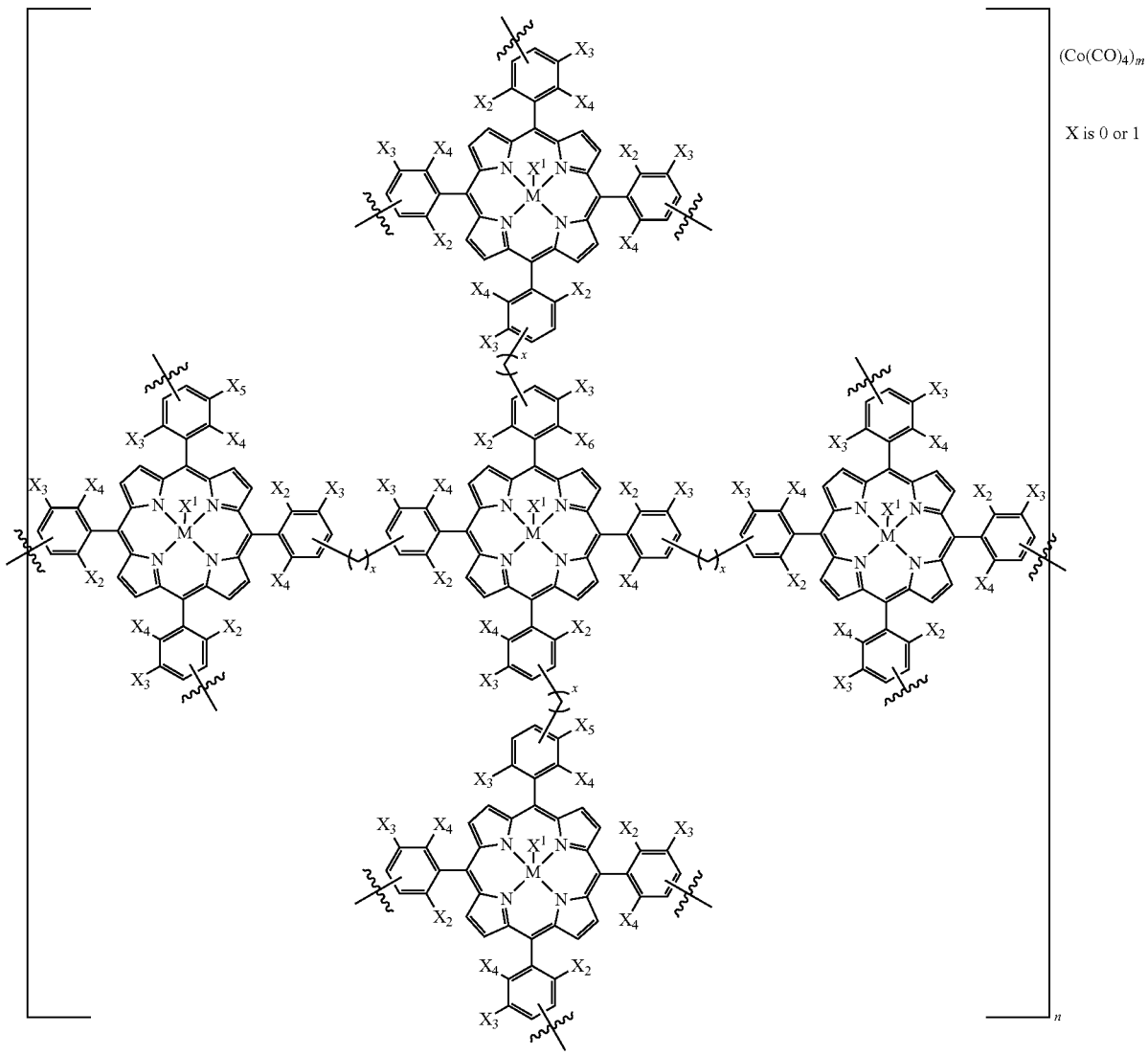

In the chemical formula (3), M is a transition metal of Al, Ir, Pt, Pd, Ru, Rh, Ni, Fe, Cu, V, Co, Cr, Au, Re, W, Zr, Mo, Ti, Th or Si, $X_1$ to $X_4$ are each independently selected from the group consisting of a hydrogen, $C_1$ to $C_{20}$ alkyl group, $C_2$ to $C_{20}$ alkenyl group, $C_2$ to $C_{20}$ alkynyl group, $C_6$ to $C_{40}$ aryl group, a phenoxy group, $C_1$ to $C_{20}$ alkoxy group, and a halogen group, X is 0 or 1, provided that a sum thereof must be 2 or more, n is an integer from 4 to 100,000, and m is an integer from 20 to 500,000.

In other aspect, the present invention relates to a method for preparing a transition metal-based heterogeneous carbonylation reaction catalyst, the method comprising the steps of: (a) synthesizing a ligand compound having three or more metal coordination numbers to which a phenyl ring capable of carrying out a Friedel-Crafts reaction is bonded; (b) synthesizing a transition metal-based homogeneous catalyst unit by reacting the ligand compound with a transition metal compound; and (c) preparing the transition metal-based heterogeneous carbonylation reaction catalyst by performing the Friedel-Crafts reaction of the transition metal-based homogeneous catalyst unit and reacting it with a counter anion-containing compound.

In an preferred embodiment of the present invention, a metalloporphyrin oligomer or polymer can be synthesized by reaction formula (1) below:

[Reaction formula (1)]
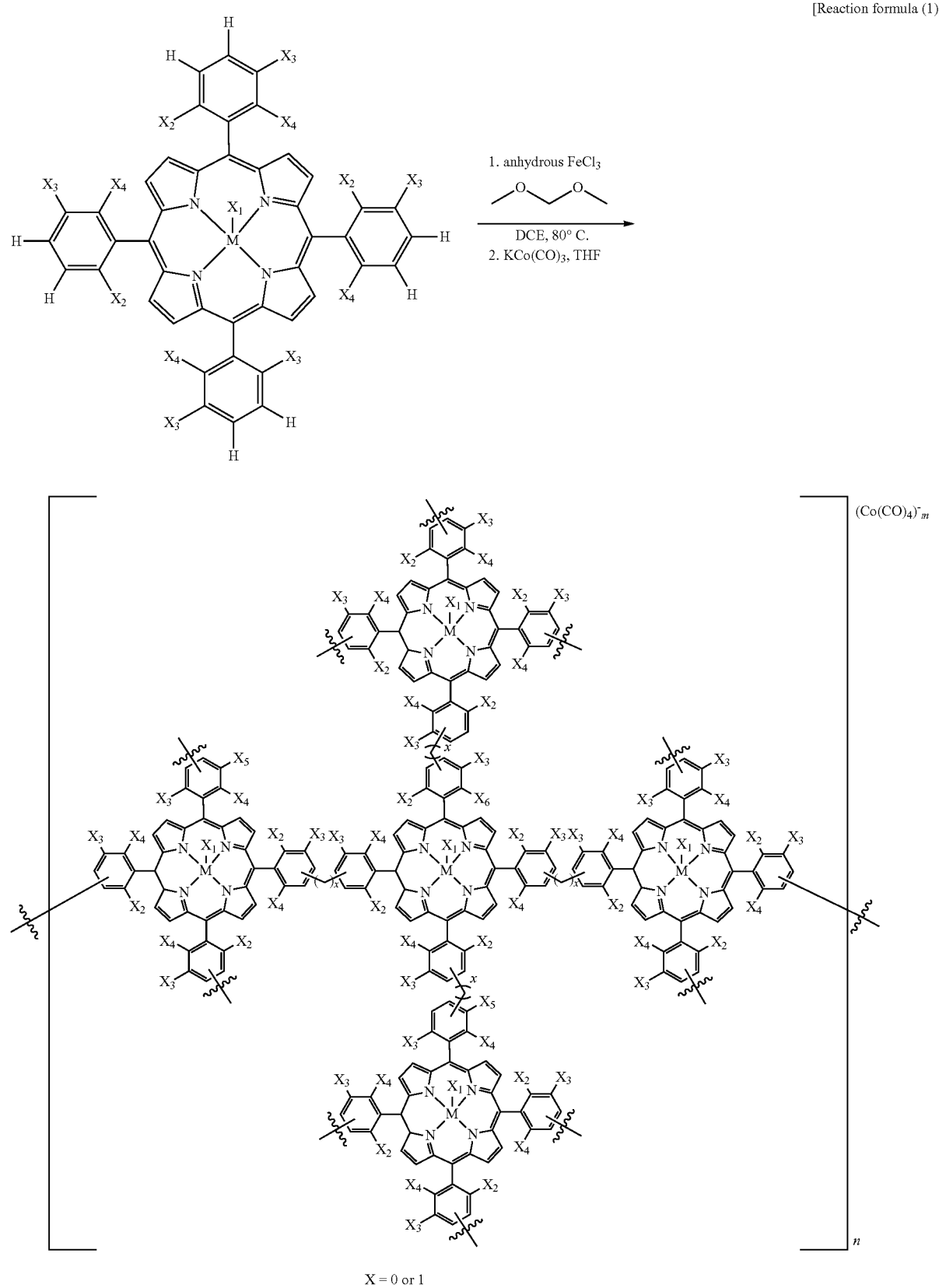
X = 0 or 1
⑦ indicates text missing or illegible when filed In the reaction formula (1), M is a transition metal of Al, Ir, Pt, Pd, Ru, Rh, Ni, Fe, Cu, V, Co, Cr, Au, Re, W, Zr, Mo, Ti, Th or Si, $X_1$ to $X_4$ are each independently selected from the group consisting of a hydrogen, $C_1$ to $C_{20}$ alkyl group, $C_2$ to $C_{20}$ alkenyl group, $C_2$ to $C_{20}$ alkynyl group, $C_6$ to $C_{40}$ aryl group, a phenoxy group, $C_1$ to $C_{20}$ alkoxy group, and a halogen group, X is 0 or 1, provided that a sum thereof must be 2 or more, n is an integer from 4 to 100,000, and m is an integer from 20 to 500,000.

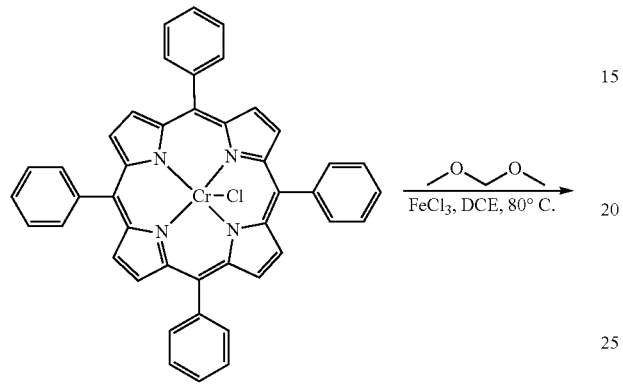

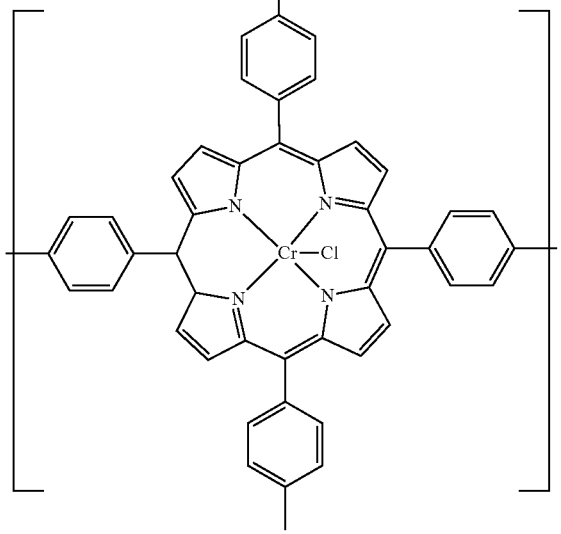

In an preferred embodiment of the present invention, an aluminum phthalocyanine oligomer or polymer can be synthesized by reaction formula (2) below:

[Reaction formula (2)]

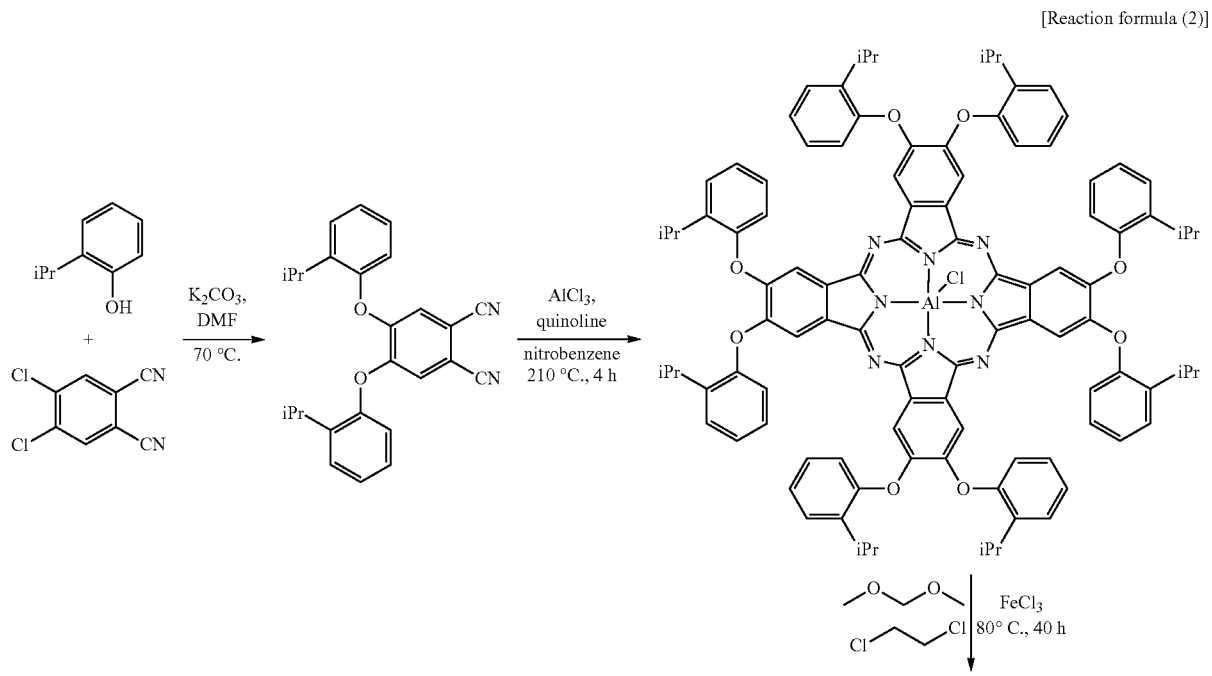

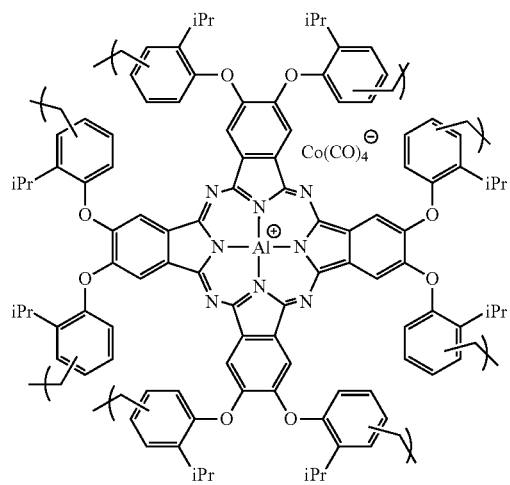 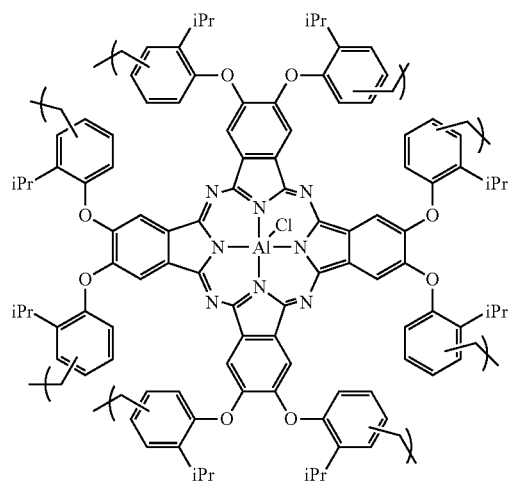

According to the reaction formula (2), the transition metal-based heterogeneous carbonylation reaction catalyst (crosslinked phthalocyanine derivative) can be prepared by the steps of synthesizing a ligand compound (phthalocyanine ligand) having three or more metal coordination numbers to which a phenyl ring (iPr-phenyl) capable of carrying out a Friedel-Crafts reaction is bonded, and synthesizing a transition metal-based homogeneous catalyst unit by reacting the ligand compound with a transition metal compound; and (c) performing the Friedel-Crafts reaction of the transition metal-based homogeneous catalyst unit (aluminum phthalocyanine derivative, AlPcCl) and reacting it with a counter anion-containing compound.

In the reaction formula (2), as the phenyl ring that can perform the Friedel-Crafts reaction and is bonded to the phthalocyanine ligand, the phenyl ring having an isopropyl group bonded thereto is bonded.

In the method for preparing the transition metal-based heterogeneous carbonylation reaction catalyst according to the present invention, a size of the transition metal-based heterogeneous carbonylation reaction catalyst can be controlled by adjusting a reaction time of the Friedel-Crafts reaction. Depending on the reaction time, a polymer of several μm can be prepared from an oligomer of 100 nm. The reaction time may be carried out for 3 to 24 hours.

It was also confirmed from the present invention that, when PO is carbonylated with β-butylurolactone using a catalyst having an excellent catalytic conversion rate of [bpy-CTF-Al(OTf)$_2$][Co(CO)$_4$] as a non-homogenized catalyst, lactone or succinic anhydride showing a high selectivity of 99% or more can be prepared by carbonylating ethylene oxide or epoxides.

Accordingly, in another aspect, the present invention relates to a method for preparing lactone, characterized by carbonylating epoxide and carbon monoxide in a solvent using the carbonylation reaction catalyst.

In still another aspect, the present invention relates to a method for preparing succinic anhydride by carbonylating lactone and carbon monoxide in a solvent using the carbonylation reaction catalyst.

In the present invention, the carbonylation reaction includes a carbonylation process of ethylene oxide series or epoxides material, and reacts with carbon monoxide to produce a lactone compound through the carbonylation, and then reacts with additional carbon monoxide to produces succinic anhydride through double carbonylation.

The epoxide can be represented by chemical formula (6) below:

[Chemical formula (6)]

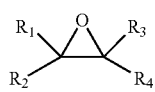

In the above formula, $R_1$, $R_2$, $R_3$ and $R_4$ are each independently a hydrogen, straight-chain or branched-chain alkyl, allyl, alkenyl, vinyl, aryl, alkylether, arylether, alkylester, arylester, cyclic ether, cyclic ester, thiol, silyl, amine, amide, nitro, cyano, thioether, thioalkyl, sulfonyl, a halogen or a hydroxy, wherein the alkyl has carbon atoms of 1 to 20, the allyl, the alkenyl and the vinyl have carbon atoms of 2 to 20, and the aryl has carbon atoms of 6 to 40.

In the present invention, the epoxide may be one or more selected from the group consisting of ethylene oxide, propylene oxide, epichlorohydrin, epibromohydrin, 1,2-epoxybutane, 2-vinyloxirane, cyclooctene oxide, 1,2-epoxy-1-carbonitrile, 1,2-epoxydodecane, n-butyl glycidylether, 2,3-epoxypropyl phenyl ether and styrene oxide, and the epoxide may preferably be ethylene oxide or propylene oxide.

The solvent may be selected from the group consisting of dimethoxy ethane (DME), tetrahydrofuran, dioxane, diglyme, tetraethylene glycol dimethylether, diethylether, 2-(2-methoxyethoxy)ethanol and anisole.

The method for preparing the lactone or the succinic anhydride according to the present invention can be carried out at a temperature of 20 to 120° C., preferably 60 to 90° C., and a CO pressure of 0.1 to 30 MPa, preferably 5 to 8 MPa.

If carbonylation of the PO using the catalyst is carried out in a stainless tube reactor containing a weakly coordinated polar solvent (for example, dimethoxy ethane, DME), which is the best solvent for carbonylation of the epoxide with the lactone, the PO is converted to β-butylolactone with the selectivity of 99% or more.

Further, subsequently, a simple filtration is performed to separate the catalyst (4) from the reaction mixture. The separated (recovered) catalyst is still active so that it can act as a catalyst for further carbonylation, and also has the activity and selectivity comparable to those of a homogeneous catalyst.

Therefore, the catalyst according to the present invention can be easily separated from the product and be reused many times, which means that the carbonylation of epoxide can be continuously carried out on an industrial scale using the heterogeneous catalyst.

EXAMPLE

Hereinafter, the present invention will be described in more detail through Examples. It will be apparent to those skilled in the relevant art that these Examples are only to illustrate the invention and are not to be construed as limiting the scope of the invention by these Examples.

EXAMPLE

A metalloporphyrin oligomer or polymer was synthesized by the reaction formula (1).

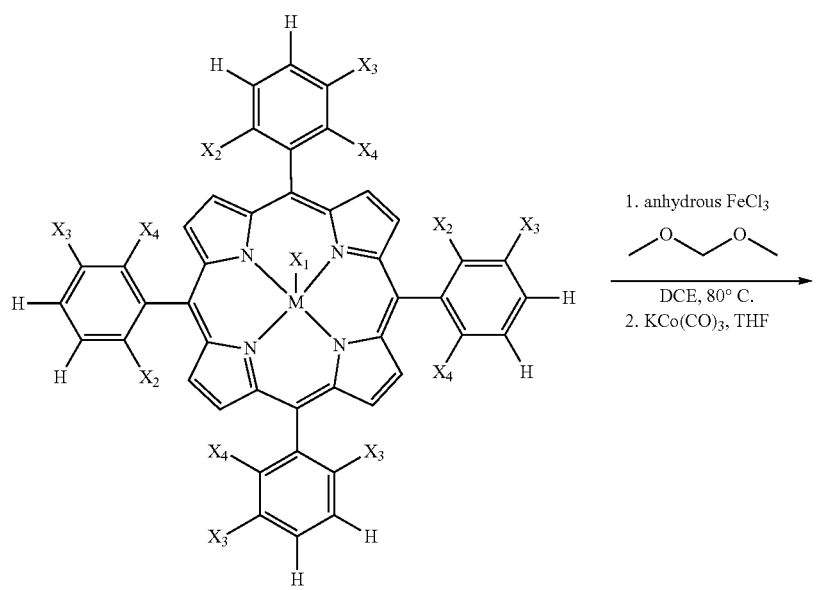

[Reaction formula (1)]

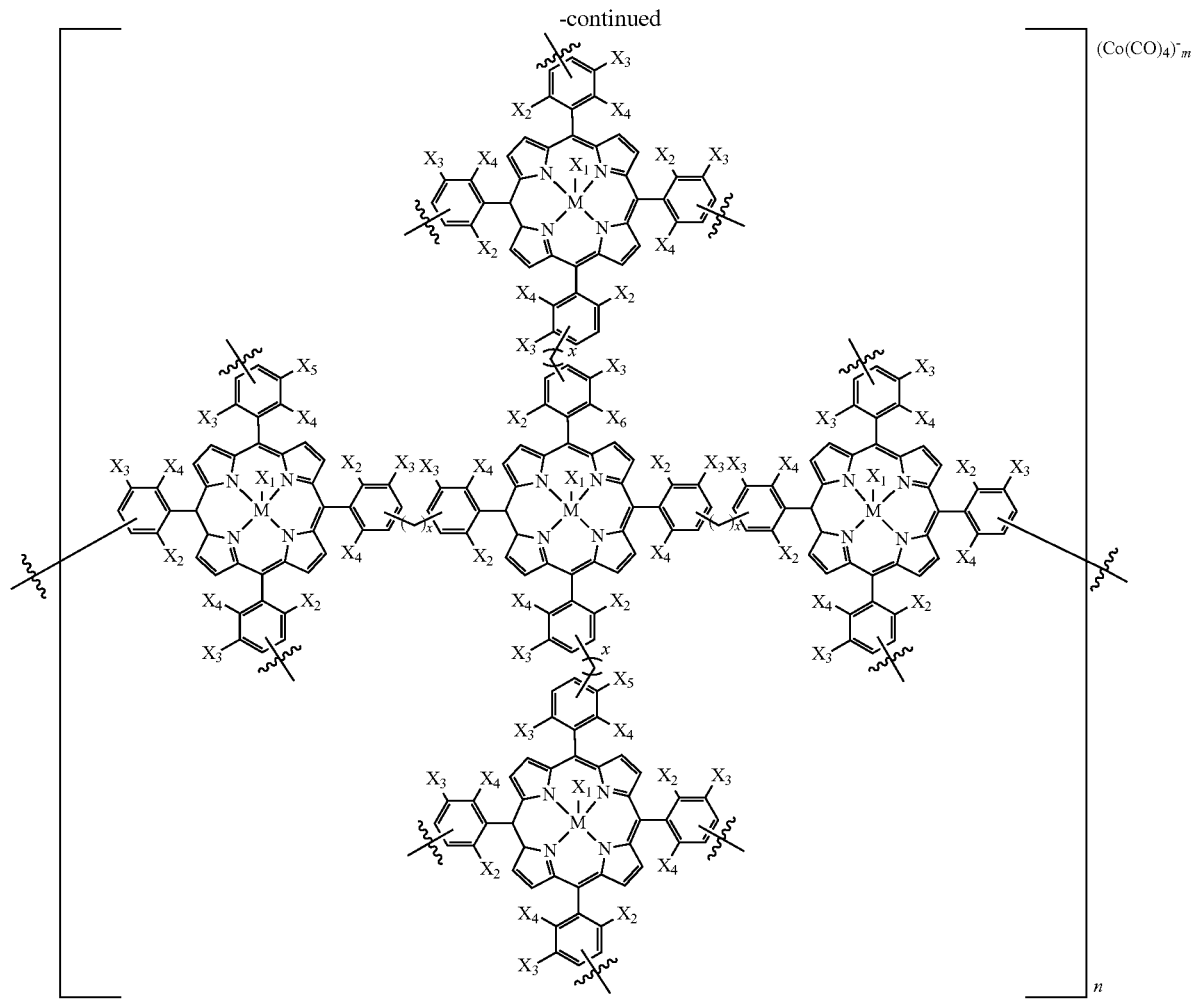

X = 0 or 1

? indicates text missing or illegible when filed

In the reaction formula (1), The left material TPPCrCl refers to a monomer before oligomer or polymerization. Subsequently, the reaction was proceeded to the right with a Friedel Kraft reaction to convert the monomer into an oligomer or polymer material (Oli-TPPCrCl-3, 6, 12 h, the right material in the reaction formula (1)), and then all of the polymerized materials were prefixed with Oli-.

The reaction was proceeded in two steps of (1) synthesis of porphyrin-based POM and (2) synthesis of $Co(CO)_4$/porphyrin-based POM catalyst.

Preparation Example 1: Synthesis of Porphyrin-Based POM

Preparation Example 1-1: Synthesis of [Oli-TPPCrCl-3h]

A porphyrin-based POM [Oli-TPPCrCl-3h] was prepared according to the reaction formula (1).

Anhydrous $FeCl_3$ (0.1226 g, 0.7558 mmol), TPPCrCl (0.1321 g, 0.1897 mmol) and dimethoxymethane (0.0575 g, 0.7567 mmol) was added in a round-bottom flask of 50 mL containing anhydrous 1,2-dichloroethane (10 mL) at a room temperature. The reaction mixture was stirred at 80° C. for 3 hours (The TPPCrCl was green and the reaction mixture was reddish brown), and cooled to the room temperature. Subsequently, all the solvents were removed from the reaction mixture, which was then washed with water and pentane and dried under a vacuum at 60° C. for 24 hours. As a result, a black precipitate with 80% in methanol (reddish brown) (0.11 g) was obtained.

Preparation Example 1-2: Synthesis of [Oli-TPPCrCl-6h]

[Oli-TPPCrCl-6h] was synthesized in the same manner as in Preparation Example 1-1, except that the stirring time in Preparation Example 1-1 was changed to 6 hours instead of 3 hours.

Preparation Example 1-3: Synthesis of [Oli-TPPCrCl-12h]

[Oli-TPPCrCl-12h] was synthesized in the same manner as in Preparation Example 1-1, except that the stirring time in Preparation Example 1-1 was changed to 12 hours instead of 3 hours.

Preparation Example 1-4: Synthesis of [Oli-TPPCrCl-24h]

[Oli-TPPCrCl-24h] was synthesized in the same manner as in Preparation Example 1-1, except that the stirring time in Preparation Example 1-1 was changed to 24 hours instead of 3 hours.

Preparation Example 2: Synthesis of Co(CO)$_4$/Porphyrin-Based POM Catalyst

Preparation Example 2-1: Synthesis of [Oli-TPPCr-3h][Co(CO)$_4$]

Inside a glass box, KCo(CO)$_4$ (0.2 g) was added to Oli-TPPCrCl-3h (Preparation Example 1-1, 0.1167 g) in a dry THE of 5 mL (a black precipitate was introduced into a solution). After the solution having black dispersed was stirred at a room temperature for 24 hours, the black reaction precipitate was filtered, and the precipitate was washed with a solvent mixture of 80% hexane and 20% THE (50 mL) and dried completely (~0.127 g).

Preparation Example 2-2: Synthesis of [Oli-TPPCr-6h][Co(CO)$_4$]

Inside a glass box, KCo(CO)$_4$ (0.8693 g) was added to Oli-TPPCrCl-6h (Preparation Example 1-2, 0.2281 g) in a dry THE of 5 mL (a black precipitate was introduced into a solution). After the solution having black dispersed was stirred at a room temperature for 24 hours, the black reaction precipitate was filtered, and the precipitate was washed with a THE (15 mL) and dried completely (~0.23 g).

Preparation Example 2-3: Synthesis of [Oli-TPPCr-12h][Co(CO)$_4$]

Inside a glass box, KCo(CO)$_4$ (1.0617 g) was added to Oli-TPPCrCl-12h (Preparation Example 1-3, 0.3043 g) in a dry THE of 5 mL (a black precipitate was introduced into a solution). After the solution having black dispersed was stirred at a room temperature for 24 hours, the black reaction precipitate was filtered, and the precipitate was washed with a THE (15 mL) and dried completely (~0.31 g).

Preparation Example 2-4: Synthesis of [Oli-TPPCr-24h][Co(CO) 4]

Inside a glass box, KCo(CO)$_4$ (1.0617 g) was added to Oli-TPPCrCl-24h (Preparation Example 1-4, 0.3043 g) in a dry THE of 5 mL (a black precipitate was introduced into a solution). After the solution having black dispersed was stirred at a room temperature for 24 hours, the black reaction precipitate was filtered, and the precipitate was washed with a THE (15 mL) and dried completely (~0.31 g).

[Reaction formula (1)]

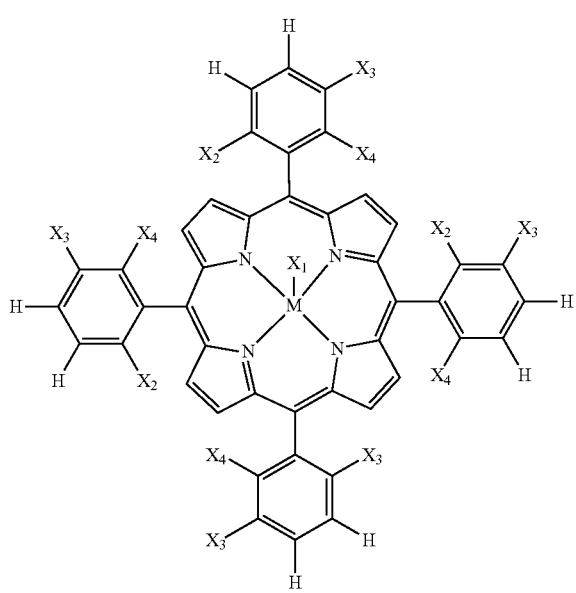
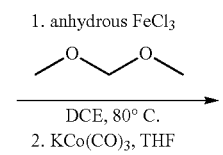

1. anhydrous FeCl$_3$
DCE, 80° C.
2. KCo(CO)$_3$, THF

-continued

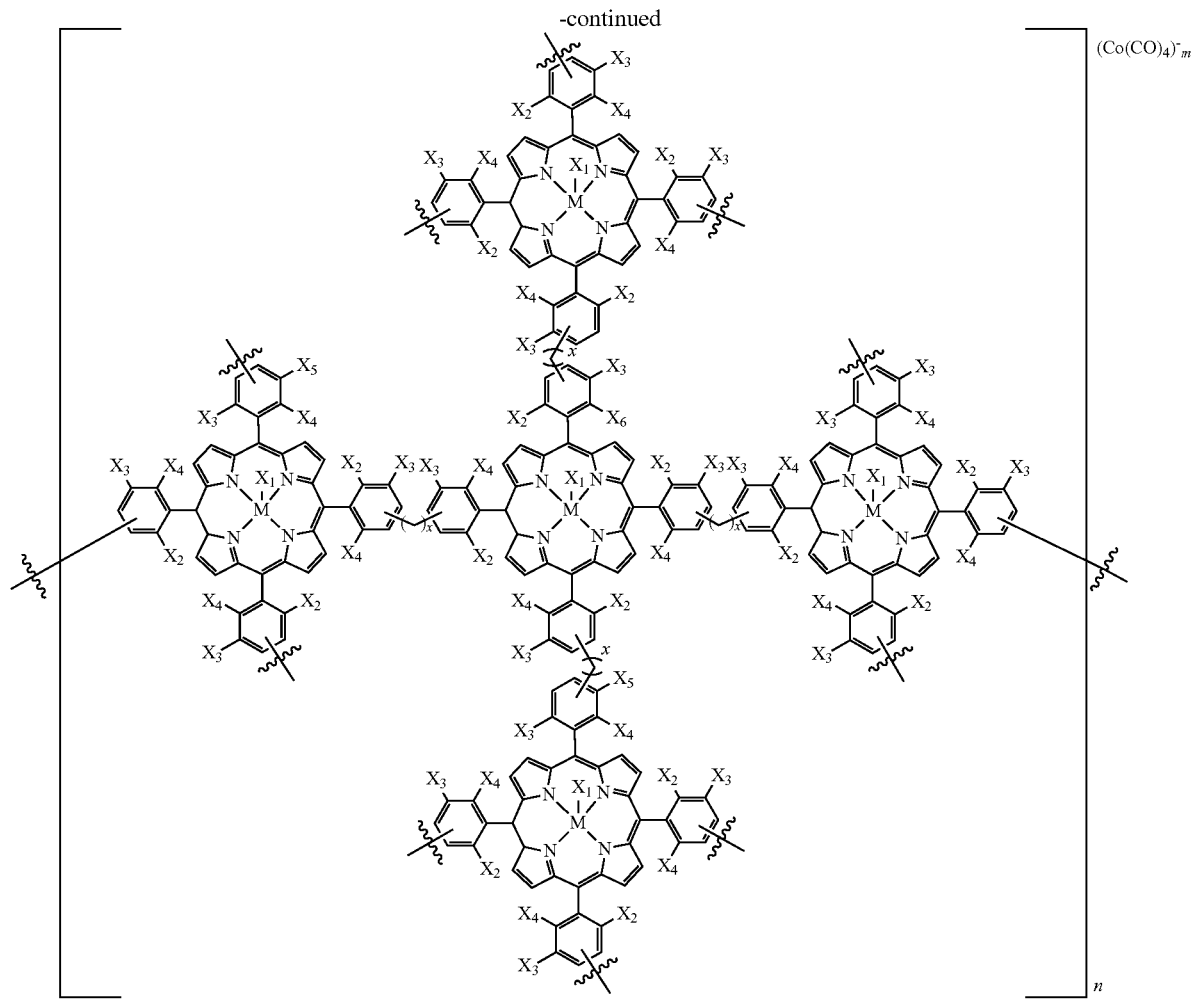

X = 0 or 1

? indicates text missing or illegible when filed

A SEM photograph of the obtained POM was shown in FIG. 1.

Example 1: Catalytic Reaction of Epoxide Carbonylation Using Porphyrin-Based POM Carbonylation reaction of polypropylene oxide using [Oli-TPPCr-3h][Co(CO)$_4$], [Oli-TPPCr-6h][Co(CO)$_4$], [Oli-TPPCr-12h][Co(CO)$_4$] and [Oli-TPPCr-24h][Co(CO)$_4$] catalysts According to reaction formula 5 below, carbonylation reaction of epoxide was performed using a porphyrin-based POM:

[Reaction formula 5]

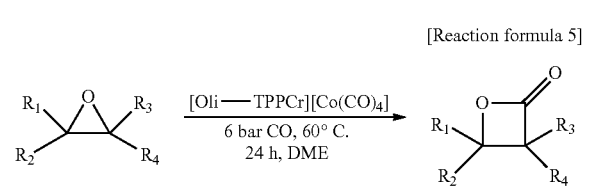

Inside a glove box, [Oli-TppCr][Co(CO)$_4$] (~0.006 g) and propylene oxide (~2.4 g) were added to DME of 2.5 mL contained in a tube reactor. The reactor was taken out of the glove box and immediately purged with CO of ~5 bar. The reactor was pressurized to CO of 60 bar, stirred at 60° C., and raised to a pressure of 62 bar. After the reaction time, the reactor was cooled to a room temperature and reduced to the pressure of about 60 bar. The CO was released from an inside of a hood, a crude sample was filtered and weighed, and then NMR was measured in CDCl$_3$ by IS (internal standard).

As shown in Table 1 and Table 2 below, the heterogeneous catalyst according to the present invention indicated an excellent activity at the mild condition (6.0 MPa and 60° C.) regardless of the reaction time, and a high selectivity of 99% or more in ring expansion carbonylation that converts the PO to lactone.

TABLE 1

| No. | Catalyst | Reaction condition | | | | | Selectivity | | | |
|---|---|---|---|---|---|---|---|---|---|---|
| | | CO bar | Temp (° C.) | Time (h) | Solvent | PO | Conversion | Lactone | Acetone | PHB | anhydride |
| 1 | [Oli-TPPCr-3 h][Co(CO)$_4$] | 60 | 60 | 24 | DME | 10000 | >43 | >99 | <1 | — | <1 |
| 2 | [Oli-TPPCr-6 h][Co(CO)$_4$] | 60 | 60 | 24 | DME | 10000 | >38 | >99 | <1 | — | <1 |
| 3 | [Oli-TPPCr-12 h][Co(CO)$_4$] | 60 | 60 | 24 | DME | 10000 | >37 | >99 | <1 | — | <1 |
| 4 | [Oli-TPPCr-24 h][Co(CO)$_4$] | 60 | 60 | 24 | DME | 10000 | >37 | >99 | <1 | — | <1 |

TABLE 2

Carbonylation with 4000-4500 equiv. of PO

| Sl. No | Catalyst | Reaction condition | | | | | Selectivity | | | |
|---|---|---|---|---|---|---|---|---|---|---|
| | | CO bar | Temp (° C.) | Time (h) | Solvent | PO | Conversion | Lactone | Acetone | PHB | anhydride |
| 1 | [Oli-TPPCr-3 h][Co(CO)$_4$] | 60 | 60 | 24 | DME | 4500 | >99 | >98 | <1 | — | 1 |
| 2 | [Oli-TPPCr-6 h][Co(CO)$_4$] | 60 | 60 | 24 | DME | 4500 | >99 | >99 | <1 | — | <1 |
| 3 | [Oli-TPPCr-12 h][Co(CO)$_4$] | 60 | 60 | 24 | DME | 4000 | >99 | >99 | <1 | — | <1 |
| 4 | [Oli-TPPCr-24 h][Co(CO)$_4$] | 60 | 60 | 24 | DME | 4000 | >99 | >99 | <1 | — | <1 |

Cat: ~0.006 g
PO: 0.96-1.08 g

As a result of checking the selectivity according to the reaction time of the carbonylation in Table 3 below, it was confirmed that the selectivity gradually increased as time lapses and the lactone selectivity reached 99% when the reaction was performed for about 24 hours.

TABLE 3

Carbonylation with 4000 equiv. of PO at different time interval

| | Catalyst | | | | | | | | | | |
|---|---|---|---|---|---|---|---|---|---|---|---|
| | [Oli-TPPCr-3 h][Co(CO)$_4$] | | | [Oli-TPPCr-6 h][Co(CO)$_4$] | | | [Oli-TPPCr-12 h][Co(CO)$_4$] | | | [Oli-TPPCr-24 h][Co(CO)$_4$] | | |
| Time (h) | lac | Acet | anhy | lac | acet | anhy | Lac | acet | anhy | lac | acet | anhy |
| 1 | 41 | 1 | 1 | 34 | 1 | 1 | 27 | <1 | <1 | 26 | <1 | <1 |
| 2 | 52 | 1 | <1 | 44 | 2 | 1 | 36 | <1 | <1 | 35 | <1 | <1 |
| 4 | 69 | <1 | <1 | 55 | 1 | 1 | 46 | <1 | <1 | 43 | <1 | <1 |
| 8 | 81 | <1 | <1 | 70 | 1 | 3 | 59 | <1 | <1 | 56 | <1 | 4 |
| 12 | 94 | <1 | <1 | 89 | 2 | 2 | 77 | <1 | <2 | 74 | <1 | 3 |
| 16 | 99 | <1 | <1 | 99 | <1 | <1 | 86 | <1 | <2 | 84 | <1 | 2 |
| 20 | 99 | <1 | 1 | 99 | <1 | <1 | 97 | <1 | <1 | 96 | <1 | 1 |
| 24 | 99 | <1 | 1 | 99 | <1 | <1 | 99 | <1 | <1 | 99 | <1 | 1 |

Cat: ~0.006 g
PO: 0.96 g

Example 2: Synthesis of Phthalocyanine-Based POM

The synthesis of the phthalocyanine-based POM catalyst was proceeded in the four steps of: (1) synthesis of a ligand, (2) synthesis of an aluminum phthalocyanine derivative (PcAlCl), (3) synthesis of a crosslinked phthalocyanine derivative, and (4) synthesis of [Poly-PcAlCl][Co(CO)$_4$].

The phthalocyanine-based POM [Poly-PcAlCl][Co(CO)$_4$] was prepared according to the reaction formula (2).

[Reaction formula (2)]
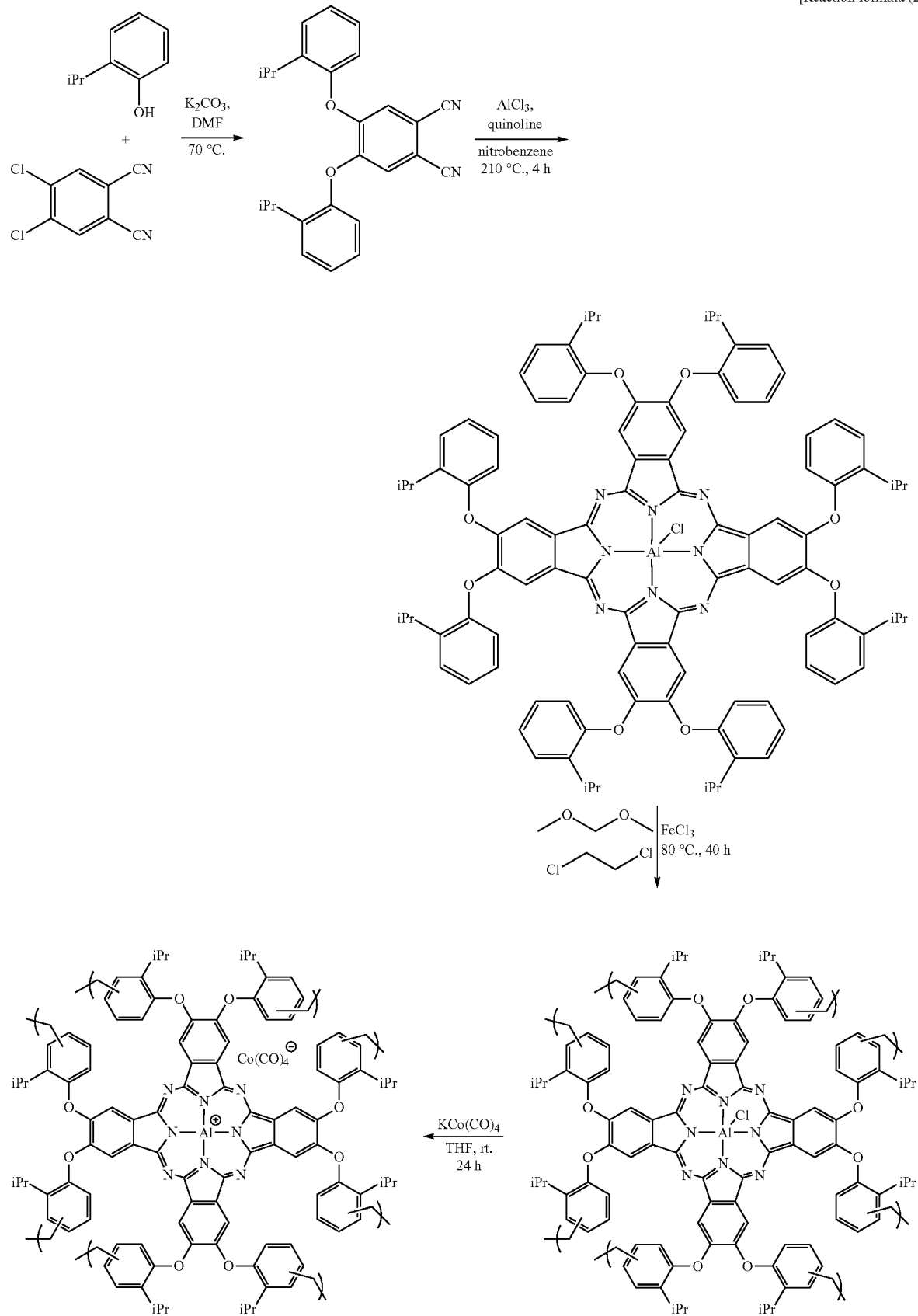

Step 1: Synthesis of Ligand

The ligand was synthesized according to the reaction formula (3).

[Reaction formula (3)]

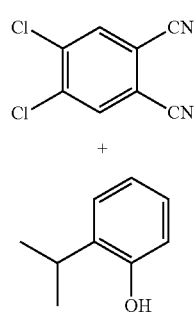

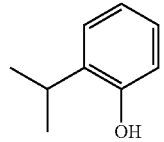

4,5-dichlorophthalonitrile (1.97 g, 0.01 mol), 2-isopropylphenol (3.41 g, 0.025 mol, 2.5 eq) and $K_2CO_3$ (11.04 g, 0.08 mol, 8 equ.) was added to a dry DMF (12 ml), and stirred in an $N_2$ atmosphere at 70 V for 36 hours. The reaction mixture was added to water (100 ml) while cooling. The produced precipitate was filtered and washed with water, and then dried under a vacuum overnight at 50° C. Recrystallization from methanol gave a light blue solid (2.5 g, 63%). 1H NMR shown in FIG. 3 indicated a compound of chemical formula (4) below:

[Chemical formula (4)]

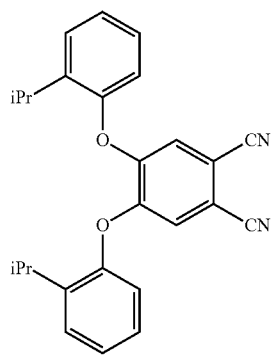

Step 2: Synthesis of Aluminum Phthalocyanine Derivative (PcAlCl)

The phthalocyanine derivative was synthesized according to reaction formula (4) below:

[Reaction formula (4)]

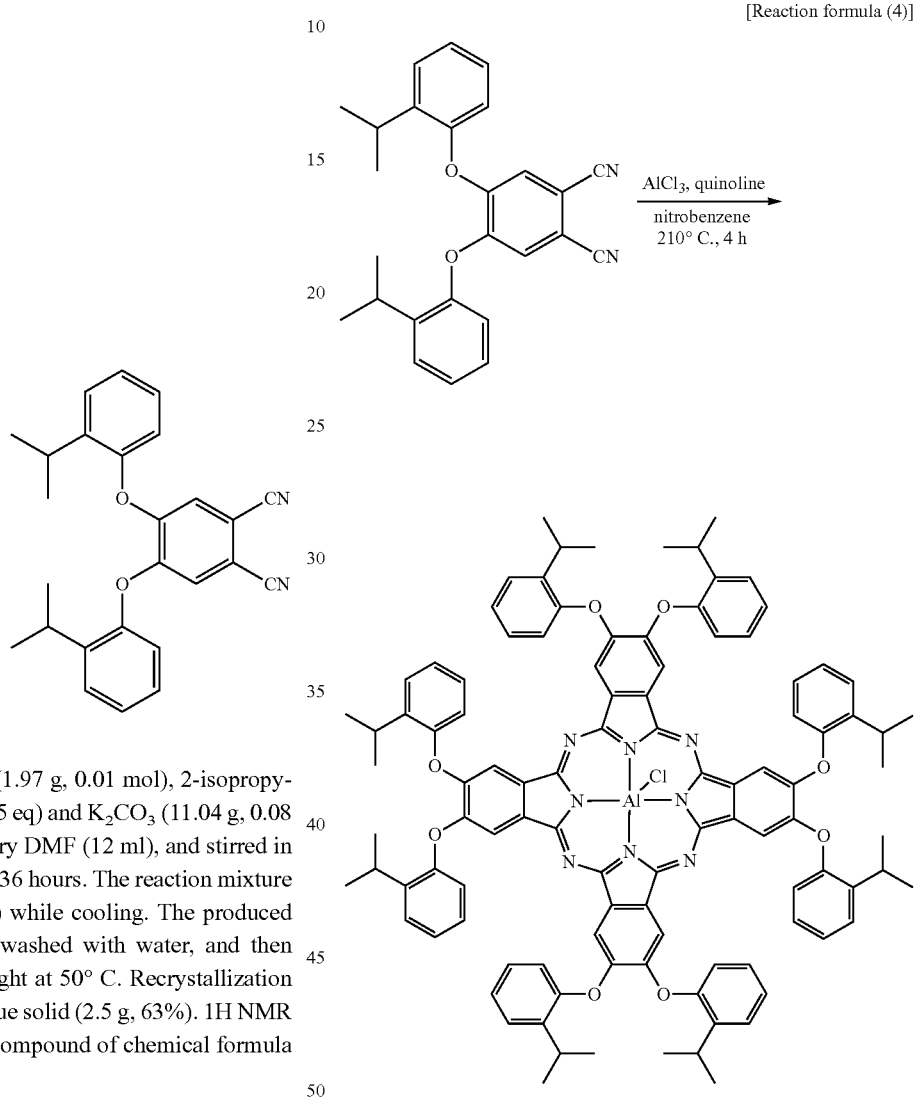

In a round bottom flask of 25 mL, 4,5-bis(2-iso-propylphenoxy)phthalonitrile of 2.376 g (0.006 mol) was added to a solvent mixture of quinoline (0.75 mL) and nitrobenzene (1.2 mL). The solution was cooled in an ice bath to 0° C. and $AlCl_3$ of 0.209 g (0.00157 mol) was added to the mixture. The reaction was refluxed at 210° C. and stirred under $N_2$ for 4 hours. The produced blue-green solution was cooled to a room temperature. The crude product was washed with hexane and purified by a column chromatography on $SiO_2$ eluting with $CH_2Cl_2/CH_3OH$ (20:1) to obtain a dark green solid compound. H NMR shown in FIG. 4 indicated a compound of chemical formula (5) (AlPcCl) below:

[Chemical formula (5)]

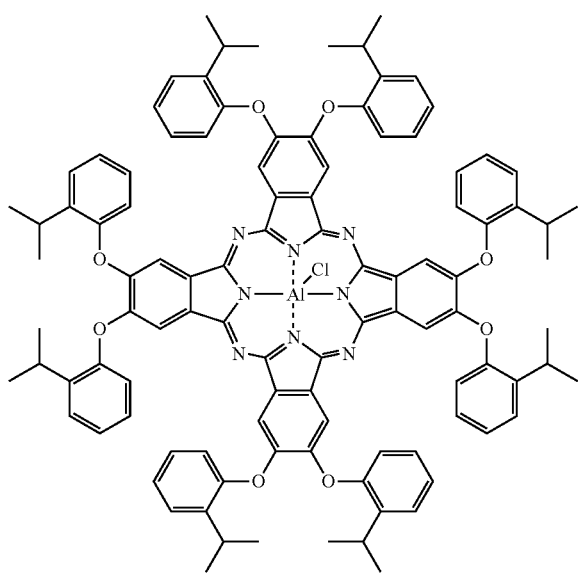

Step 3: Synthesis of Crosslinked Phthalocyanine Derivative

Anhydrous FeCl₃ (197 mg) was added to a three-neck flask of 50 mL containing a mixture of PcAlCl (510 mg) and formaldehyde dimethylacetal (92 mg) dissolved in anhydrous 1,2-dichloroethane (8 mL) under a N₂ atmosphere. The reaction was stirred at 80° C. for 40 hours, and then cooled to a room temperature. The resulting precipitate was filtered and washed with water, methanol, CH₂Cl₂, acetone and THF, respectively. The produced polymer was further purified by Soxhlet extractions for 36 hours using the THF as a solvent. After drying under a vacuum at 130° C. overnight, a product of dark blue powder (389 mg) was obtained.

A SEM photograph of the product was shown in FIG. 5.

Step 4: Synthesis of [Poly-PcAlCl][Co(CO)₄]

Inside a glove box, KCo(CO)₄ (260 mg, 8 equ.), Poly-PcAlCl (385 mg) and THE (8 mL) were mixed in a vial. After stirring at a room temperature for 24 hours, the solution was filtered and washed several times with the THF. A product (390 mg) was obtained after drying under a vacuum.

Summarizing the above results, the heterogeneous carbonylation reaction catalyst in which the transition metal-based homogeneous catalyst unit was crosslinked through the Friedel-Crafts reaction was synthesized. The heterogeneous catalyst showed an excellent activity at a mild condition (6.0 MPa and 60° C.) and a high selectivity of 90% in the ring expansion carbonylation that converts the PO to lactone. Further, the activity and the selectivity of the heterogeneous catalyst are comparable to those of the homogeneous catalyst. In addition, the heterogeneous catalyst is easily separated from the product and can be reused several times. This results mean that the heterogeneous catalyst can continuously perform carbonylation of the epoxide on an industrial scale.

INDUSTRIAL AVAILABILITY

The carbonylation reaction catalyst according to the present invention is easily separated from the product while having a catalytic efficiency equal to or higher than that of the conventional catalyst including the homogeneous system, is stable to an acid, a base and a temperature, and does not reduce the catalytic efficiency even when reused, thereby being useful for mass production of β-lactone, as a carbonylation reaction catalyst using a carbon dioxide.

From the specific portions of the present invention described in detail above, it will be apparent to a person who has an ordinary knowledge in the art that these specific techniques are merely preferred embodiments and the scope of the present invention is not limited thereby. Accordingly, it will be said that the substantial scope of the present invention is defined by the appended claims and their equivalents.

What are claimed are:

1. A transition metal-based heterogeneous carbonylation reaction catalyst, wherein a transition metal-based homogeneous catalyst unit represented by Chemical formula (1) below is bonded through a Friedel-Crafts reaction:

M(L-R$_n$)X      Chemical Formula (1)

in Chemical formula (1), M is a transition metal of Al, Ir, Pt, Pd, Ru, Rh, Ni, Fe, Cu, V, Co, Cr, Au, Re, W, Zr, Mo, Ti, Th or Si, L is a ligand having three or more metal coordination numbers, R is a phenyl ring capable of carrying out the Friedel-Crafts reaction, n is an integer of 2 or more, and X is a counter anion of [Co(CO)₄]⁻.

2. The transition metal-based heterogeneous carbonylation reaction catalyst according to claim 1, wherein the L is phthalocyanine, porphyrin, salen, or salphen.

3. The transition metal-based heterogeneous carbonylation reaction catalyst according to claim 1, wherein the R is represented by Chemical formula (2) below:

Chemical formula (2)

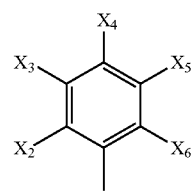

in Chemical formula (2), X₂ to X₆ are each independently selected from the group consisting of a hydrogen, C₁ to C₂₀ alkyl group, C₂ to C₂₀ alkenyl group, C₂ to C₂₀ alkynyl group, C₆ to C₄₀ aryl group, a phenoxy group, C₁ to C₂₀ alkoxy group, and a halogen group, provided that at least one of them should be a hydrogen.

4. The transition metal-based heterogeneous carbonylation reaction catalyst according to claim 1, represented by Chemical formula (3) below:

Chemical formula (3)

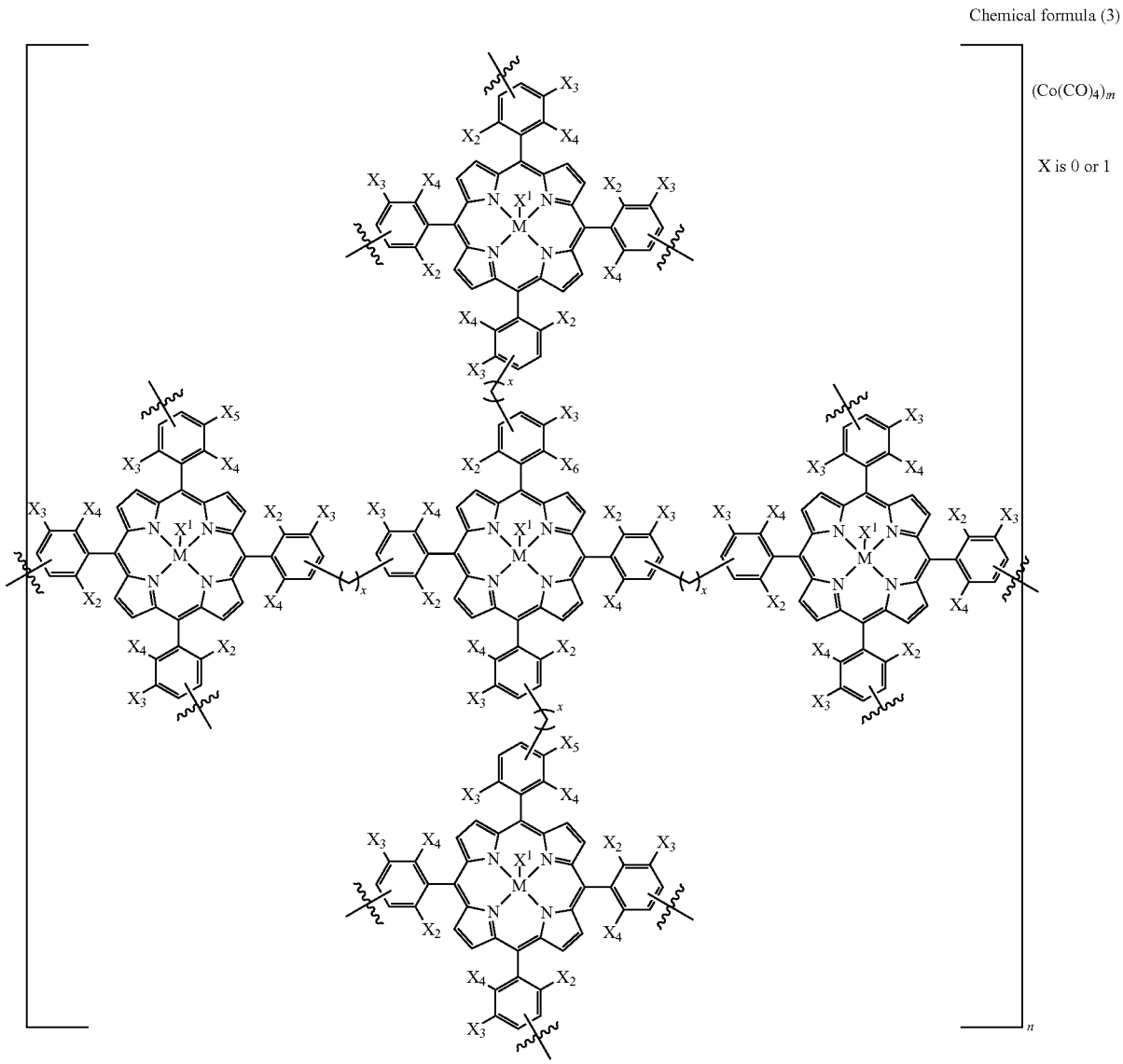

in Chemical formula (3), M is a transition metal of Al, Ir, Pt, Pd, Ru, Rh, Ni, Fe, Cu, V, Co, Cr, Au, Re, W, Zr, Mo, Ti, Th or Si, $X_1$ to $X_4$ are each independently selected from the group consisting of a hydrogen, $C_1$ to $C_{20}$ alkyl group, $C_2$ to $C_{20}$ alkenyl group, $C_2$ to $C_{20}$ alkynyl group, $C_6$ to $C_{40}$ aryl group, a phenoxy group, $C_1$ to $C_{20}$ alkoxy group, and a halogen group, X is 0 or 1, provided that a sum thereof must be 2 or more, n is an integer from 4 to 100,000, and m is an integer from 20 to 500,000.

5. A method for preparing lactone, comprising carbonylating an epoxide and a carbon monoxide in a solvent in the presence of the catalyst of claim 1.

6. The method for preparing the lactone according to claim 5, wherein the epoxide is represented by Chemical formula (6) below:

Chemical formula (6)

in Chemical formula (6), $R_1$, $R_2$, $R_3$ and $R_4$ are each independently a hydrogen, straight-chain or branched-chain alkyl, allyl, alkenyl, vinyl, aryl, alkylether, arylether, alkylester, arylester, cyclic ether, cyclic ester, thiol, silyl, amine, amide, nitro, cyano, thioether, thioalkyl, sulfonyl, a halogen or a hydroxy, wherein the alkyl has carbon atoms of 1 to 20, the allyl, the alkenyl and the vinyl have carbon atoms of 2 to 20, and the aryl has carbon atoms of 6 to 40.

7. The method for preparing the lactone according to claim 5, wherein the epoxide is one or more selected from the group consisting of ethylene oxide, propylene oxide, epichlorohydrin, epibromohydrin, 1,2-epoxybutane, 2-vinyloxirane, cyclooctene oxide, 1,2-epoxy-1-carbonitrile, 1,2-epoxydodecane, n-butyl glycidylether, 2,3-epoxypropyl phenyl ether, and styrene oxide.

8. The method for preparing the lactone according to claim 5, wherein the solvent is selected from the group consisting of dimethoxy ethane (DME), tetrahydrofuran, dioxane, diglyme, tetraethylene glycol dimethyl ether, diethylether, 2-(2-methoxyethoxy)ethanol, and anisole.

9. The method for preparing the lactone according to claim 5, wherein the method is performed at a temperature of 20 to 120° C. and a CO pressure of 0.1 to 30 MPa.

10. A method for preparing succinic anhydride, comprising carbonylating a lactone and a carbon monoxide in a solvent in the presence of the catalyst of claim 1.

11. The method for preparing the succinic anhydride according to claim 10, wherein the lactone is represented by Chemical formula (7) below:

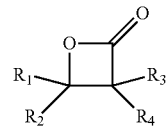

Chemical formula (7)

in Chemical formula (7), $R_1$, $R_2$, $R_3$ and $R_4$ are each independently a hydrogen, straight-chain or branched-chain alkyl, allyl, alkenyl, vinyl, aryl, alkylether, arylether, alkylester, arylester, cyclic ether, cyclic ester, thiol, silyl, amine, amide, nitro, cyano, thioether, thioalkyl, sulfonyl, a halogen or a hydroxy, wherein the alkyl has carbon atoms of 1 to 20, the allyl, the alkenyl and the vinyl have carbon atoms of 2 to 20, and the aryl has carbon atoms of 6 to 40.

12. The method for preparing the succinic anhydride according to claim 10, wherein the solvent is selected from the group consisting of dimethoxy ethane (DME), tetrahydrofuran, dioxane, diglyme, tetraethylene glycol dimethylether, diethylether, 2-(2-methoxyethoxy)ethanol, and anisole.

13. The method for preparing the succinic anhydride according to claim 10, wherein the method is performed at a temperature of 20 to 120° C. and a CO pressure of 0.1 to 30 MPa.

* * * * *